United States Patent
Carley et al.

(10) Patent No.: US 8,053,413 B2
(45) Date of Patent: Nov. 8, 2011

(54) METHODS FOR TREATING SLEEP DISORDERS BY CHOLECYSTOKININ (CCK) RECEPTOR B ANTAGONISTS

(75) Inventors: David W. Carley, Evanston, IL (US); Miodrag Radulovacki, Chicago, IL (US)

(73) Assignee: The Board of Trustees of the University of Illinois, Chicago, IL (US)

( * ) Notice: Subject to any disclaimer, the term of this patent is extended or adjusted under 35 U.S.C. 154(b) by 571 days.

(21) Appl. No.: 11/916,563

(22) PCT Filed: Jun. 6, 2006

(86) PCT No.: PCT/US2006/021929
§ 371 (c)(1),
(2), (4) Date: Dec. 19, 2007

(87) PCT Pub. No.: WO2006/133197
PCT Pub. Date: Dec. 14, 2006

(65) Prior Publication Data
US 2008/0200367 A1    Aug. 21, 2008

Related U.S. Application Data

(60) Provisional application No. 60/687,803, filed on Jun. 6, 2005.

(51) Int. Cl.
*A61K 38/00* (2006.01)
*A61K 31/675* (2006.01)
*A61P 25/00* (2006.01)
*A01N 43/02* (2006.01)
*A01N 43/16* (2006.01)

(52) U.S. Cl. .......... 514/17.7; 514/449; 514/459; 514/79

(58) Field of Classification Search .................. None
See application file for complete search history.

(56) References Cited

U.S. PATENT DOCUMENTS

| | | | | |
|---|---|---|---|---|
| 4,820,834 A | 4/1989 | Evans et al. | .................. | 540/504 |
| 5,618,811 A | 4/1997 | Lowe, III | .................. | 514/218 |
| 5,688,943 A | 11/1997 | Ryder et al. | .................. | 540/509 |
| 5,728,829 A | 3/1998 | Semple et al. | ................. | 540/509 |
| 5,962,451 A | 10/1999 | Ryder et al. | .................. | 514/221 |
| 6,075,033 A | 6/2000 | Makovec et al. | ............... | 514/278 |
| 2004/0198723 A1 | 10/2004 | Gibson | | |

OTHER PUBLICATIONS

Burgess et al. J of Cell Bio. 1990, 111:2129-2138.*
Bowie et al. Science, 1990, 247:1306-1310.*
Pawson et al. 2003, Science 300:445-452.*
Widdop et al., "Electrophysiological and autoradiographical evidence for cholecystokinin A receptors on rat isolated nodose gangila", J. Autonomic Nervous System 1993 46:65-73.
Yoshioka et al., "Pharmacological Characterization of 5-Hydroxytryptamine-Induced Apnea in the Rat", J. Pharmacology and Experimental Therapeutics 1992 260(2):917-924.
DeMesquita et al., "Effect of chronic intracerebroventricular infusion of cholecystokinin on respiration and sleep", Brain Research 1986 378:127-132.
Bennet et al., "Apneic effects of cholecystokinin in unanaesthetized fetal sheep", Journal of Developmental Physiology 1990 14:229-233.
Herranz, Rosario, "Cholecystokinin Antagonists; Pharmacological and Therapeutic Potential", Medicinal Research Reviews 2003 23 (5):559-605.
Fourmy et al. "Structure of Cholecystokinin Receptor Binding Sites and Mechanism of Activation/Inactivation by Agonists/Antagonists" Pharmacology & Toxicology 2002 vol. 91: 313-320.
Bock et al. "Cholecystokinin (CCK) Receptor Antagonists" Current Pharmaceutical Design Ed. Graham Johnson 1995 vol. 1(3) : 284-289.
Gales et al. "Identification of Tyrosine 189 and Asparagine 358 of the Cholecystokinin 2 Receptor in Direct Interaction with the Crucial C-Terminal Amide of Cholecystokinin by Molecular Modeling, Site Directed Mutagenesis, and Structure/Affinity Studies" Molecular Pharmacology 2003 vol. 63(5) : 973-982.

* cited by examiner

*Primary Examiner* — Chang-Yu Wang
(74) *Attorney, Agent, or Firm* — Licata & Tyrrell, P.C.

(57) ABSTRACT

The present invention relates to a method for preventing or ameliorating a sleep-related breathing disorder. The method involves the use of one or a combination of cholecystokinin (CCK) receptor antagonists.

1 Claim, No Drawings

METHODS FOR TREATING SLEEP DISORDERS BY CHOLECYSTOKININ (CCK) RECEPTOR B ANTAGONISTS

INTRODUCTION

This application claims benefit of U.S. Provisional Patent Application Ser. No. 60/687,803, filed Jun. 6, 2005, the contents of which are incorporated herein by reference in their entirety.

BACKGROUND OF THE INVENTION

Much effort has been devoted to the study of a discrete group of breathing disorders that occur primarily during sleep with consequences that may persist throughout the waking hours in the form of daytime sleepiness, and result in substantial economic loss (e.g., thousands of lost man-hours) or cause employment safety issues (e.g., employee non-attentiveness during operation of heavy-machinery). Sleep-related breathing disorders are characterized by repetitive reduction in breathing (hypopnea), periodic cessation of breathing (apnea), or a continuous or sustained reduction in ventilation.

In general, sleep apnea is defined as an intermittent cessation of airflow at the nose and mouth during sleep. By convention, apneas of at least 10 seconds in duration have been considered important; however, in most individuals, apneas are 20-30 seconds in duration and may be as long as 2-3 minutes. While there is some uncertainty as to the minimum number of apneas that should be considered clinically important, by the time most individuals come to a doctor's attention they have at least 10 to 15 events per hour of sleep.

Sleep apneas have been classified into three types: central, obstructive (the most common type), and mixed. In central sleep apnea, the neural drive to all respiratory muscles is transiently abolished. In obstructive sleep apneas, airflow ceases despite continuing respiratory drive because of occlusion of the oropharyngeal airway. Mixed apneas, which consist of a central apnea followed by an obstructive component, are a variant of obstructive sleep apnea.

Obstructive sleep apnea syndrome (OSAS) has been identified in as many as 24% of working adult men and 9% of similar women, with peak prevalence in the sixth decade. Habitual heavy snoring, which is an almost invariant feature of OSAS, has been described in up to 24% of middle-aged men, and 14% of similarly aged women, with even greater prevalence in older subjects. A definitive event of obstructive sleep apnea syndrome is the occlusion of the upper airway, frequently at the level of the oropharynx. The resultant apnea generally leads to a progressive-type asphyxia until the individual is briefly aroused from the sleeping state, thereby restoring airway patency and airflow.

The recurrent episodes of nocturnal asphyxia and of arousal from sleep that characterize OSAS lead to a series of secondary physiologic events, which in turn give rise to the clinical complications of the syndrome. The most common manifestations are neuropsychiatric and behavioral disturbances that are thought to arise from the fragmentation of sleep and loss of slow-wave sleep induced by the recurrent arousal responses. Nocturnal cerebral hypoxia also may play an important role. The most pervasive manifestation is excessive daytime sleepiness. OSAS is now recognized as a leading cause of daytime sleepiness and has been implicated as an important risk factor for such problems as motor vehicle accidents. Other related symptoms include, but are not limited to, intellectual impairment, memory loss, personality disturbances, and impotence.

The other major manifestations are cardiorespiratory in nature and are thought to arise from the recurrent episodes of nocturnal asphyxia. Most individuals demonstrate a cyclical slowing of the heart during the apneas to 30 to 50 beats per minute, followed by tachycardia of 90 to 120 beats per minute during the ventilatory phase. A small number of individuals develop severe bradycardia with asystoles of 8 to 12 seconds in duration or dangerous tachyarrhythmias, including unsustained ventricular tachycardia. OSAS also aggravates left ventricular failure in patients with underlying heart disease. This complication is most likely due to the combined effects of increased left ventricular afterload during each obstructive event, secondary to increased negative intrathoracic pressure, recurrent nocturnal hypoxemia, and chronically elevated sympathoadrenal activity.

Central sleep apnea is less prevalent as a syndrome than OSAS, but can be identified in a wide spectrum of patients with medical, neurological, and/or neuromuscular disorders associated with diurnal alveolar hypoventilation or periodic breathing. A definitive event in central sleep apnea is transient abolition of central drive to the ventilatory muscles. The resulting apnea leads to a primary sequence of events similar to those of OSAS. Several underlying mechanisms can result in cessation of respiratory drive during sleep. Defects in the metabolic respiratory control system and respiratory neuromuscular apparatus are apparent. Other central sleep apnea disorders arise from transient instabilities in an otherwise intact respiratory control system. In individuals with clinically significant central sleep apnea, the primary sequence of events that characterize the disorder leads to prominent physiological and clinical consequences. In those individuals with central sleep apnea alveolar hypoventilation syndrome, daytime hypercapnia and hypoxemia are usually evident and the clinical picture is dominated by a history of recurrent respiratory failure, polycythemia, pulmonary hypertension, and right-sided heart failure. Complaints of sleeping poorly, morning headache, and daytime fatigue and sleepiness are also prominent. In contrast, in individuals whose central sleep apnea results from an instability in respiratory drive, the clinical picture is dominated by features related to sleep disturbance, including recurrent nocturnal awakenings, morning fatigue, and daytime sleepiness.

Currently, the most common and most effective treatment for adults with sleep apnea and other sleep-related breathing disorders are mechanical forms of therapy that deliver positive airway pressure (PAP). Under PAP treatment, an individual wears a tight-fitting plastic mask over the nose when sleeping. The mask is attached to a compressor, which forces air into the nose creating a positive pressure within the patient's airways. The principle of the method is that pressurizing the airways provides a mechanical "splinting" action that prevents airway collapse and therefore, obstructive sleep apnea. Although an effective therapeutic response is observed in most patients who undergo PAP treatment, many patients cannot tolerate the apparatus or pressure and refuse treatment. Moreover, covert monitoring studies clearly demonstrate that long-term compliance with PAP treatment is very poor.

A variety of upper airway and craniofacial surgical procedures have been attempted for treatment of OSAS. While adenotonsillectomy appears to be an effective cure for OSAS in many children, upper airway surgery is rarely curative in adult OSAS patients. Surgical success is generally taken to be a 50% reduction in apnea incidence and there are no useful screening methods to identify the individuals that would benefit from the surgery versus those who would not derive a benefit.

Pharmacological treatments of several types have been attempted in patients with sleep apnea but, thus far, none have proven to be generally useful. (see Smith & Quinnell (2004) *Drugs* 64:138-1399). A number of compounds have been tested because of their expected respiratory stimulant properties. These include acetazolamide, a carbonic anhydrase inhibitor that produced variable improvement in individuals with primarily central apneas, but caused an increase in obstructive apneas; medroxyprogesterone, a progestin that has demonstrated no consistent benefit in OSAS; and theophylline, a compound usually used for the treatment of asthma that may benefit patients with central apnea, but appears to be of no use in adult patients with obstructive apnea.

Other attempted pharmacological treatments include administration of adenosine, adenosine analogs and adenosine reuptake inhibitors (see, e.g., U.S. Pat. No. 5,075,290). Specifically, adenosine, a ubiquitous compound within the body that is elevated in individuals with OSAS, has been shown to stimulate respiration and is somewhat effective in reducing apnea in an animal model of sleep apnea.

Other agents for treating OSAS include compounds that stimulate brain activity or are opioid antagonists. Specifically, since increased cerebral spinal fluid opioid activity has been identified in OSAS, central stimulants or opioid antagonists are thought to be a helpful treatment of OSAS. However, doxapram, a compound that stimulates the central nervous system and carotid body chemoreceptors, while decreasing the length of apneas, does not alter the average arterial oxygen saturation in individuals with obstructive sleep apnea. Further, the opioid antagonist naloxone, which is known to stimulate ventilation, is only slightly helpful in individuals with obstructive sleep apnea.

Several agents that act on neurotransmitters and neurotransmitter systems involved in respiration have been tested in individuals with OSAS. Most of these compounds have been developed as anti-depressant medications that work by increasing the activity of monoamine neurotransmitters, including norepinephrine, dopamine, and serotonin. For example, protriptyline, a tricyclic antidepressant, has been tested in several small trials with variable results and frequent and significant side effects. As serotonin may promote sleep and stimulate respiration, tryptophan, a serotonin precursor, as well as selective serotonin reuptake inhibitors (SSRIs) have been tested in individuals with OSAS. Although the serotonin reuptake inhibitor, fluoxetine has been suggested for treating sleep apnea (U.S. Pat. No. 5,356,934), initial evidence suggests that such compounds may yield measurable benefits in only approximately 50% of individuals with OSAS. The rationale for using SSRIs such as fluoxetine or paroxetine to treat sleep apnea syndrome rests in part on their ability to stimulate upper airway motor outputs. Applications of serotonin to the floor of the fourth ventricle (Rose, et al. (1995) *Respir. Physiol.* 101:59-69) or into the hypoglossal motor nucleus (Kubin, et al. (1992) *Neurosci. Lett.* 139:243-248) produced upper airway motor activation in cats; effects that appear to be mediated predominantly by serotonin subtype 2 receptors (Okabe, et al. (1997) *Respir. Physiol.* 110: 151-160; Volgin, et al. (2003) *Eur. J. Neurosci.* 17:1179-1188). Conversely, systemic administration of 5-hydroxytryptamine 2 receptor antagonists to English bulldogs reduced electrical activation of upper airway muscles, diminishing upper airway cross-sectional area (Veasey, et al. (1996) *Am. J. Respir. Crit. Care Med.* 153:776-786). These observations provide a likely explanation for the improvements in sleep-disordered breathing observed in some patients following SSRI treatment, but illustrate that to be generally effective, SSRI treatment must be combined with another agent.

Buspirone, a specific serotonin subtype 1 receptor agonist that stimulates respiration (Mendelson, et al. (1990) *Am. Rev. Respir. Dis.* 141:1527-1530), has been shown to reduce apnea index in 4 of 5 patients with sleep apnea syndrome (Mendelson, et al. (1991) *J. Clin. Psychopharmacol.* 11:71-72) and to eliminate post-surgical apneustic breathing in one child (Wilken, et al. (1997) *J. Pediatr.* 130:89-94). The use of serotonin agonists to treat apneas has been suggested in U.S. Pat. Nos. 6,552,062; 6,433,175; 6,432,956; 6,387,907; 6,356,598; 6,380,238; and 6,303,608.

Serotonin antagonists also have been examined as drug treatments for sleep apnea in humans and in animal models of sleep-related breathing disorders. In rats that express frequent central apneas during all sleep stages, the serotonin antagonists ondansetron, R-zacopride, and mirtazapine all have been shown to reduce apnea frequency. Mirtazapine was able to reduce apnea frequency by 50% in one study of OSAS patients, whereas ondansetron failed to demonstrate any effect in another study. Nevertheless, the use of serotonin antagonists to treat OSAS has been disclosed in U.S. Pat. Nos. 6,835,740; 6,727,242; 6,649,183; 6,613,779; 6,576,670; 6,559,165; 6,552,062; 6,548,082; 6,465,490; 6,331,536; 6,303,595; 6,277,864; 6,143,792; 6,048,879; 5,995,470 and U.S. patent application Ser. No. 10/285,277.

Several other treatments for sleep apnea have been disclosed, including the administration of the nucleoside uptake blocker dipyridamole (U.S. Pat. No. 5,502,067), pilocarpine compounds (U.S. Pat. No. 5,407,953), ubidecarenone (U.S. Pat. No. 5,422,374), somatostatin receptor agonists (U.S. patent application Ser. No. 10/280,517), and acetylcholineesterase inhibitors (U.S. Pat. No. 6,034,117). Stimulation of various structures, such as the pontine intertrigeminal region (Radulovacki, et al. (2003) *Brain Research* 975:66-72; Radulovacki, et al. (2004) *Sleep* 27:383-387) and the pedunculopontine tegmentum (Saponjic, et al. (2003) *Resp. Physiol. Neurobiol.* 138:223-237) by the excitatory amino acid glutamate has been shown to evoke immediate apnea, and a glutamate release inhibitor was shown to reduce the frequency of central apneas in a rat model (Radulovacki, et al. (2001) *J. Pharm. Pharmacol.* 53:1555-9). The use of glutamate antagonists or release inhibitors to treat OSAS is disclosed in U.S. Pat. No. 6,555,564. In addition, the cannabinoid receptor agonist Δ9-tetrahydrocannibinol has been shown to reduce sleep apneas in an animal model (Carley, et al. (2002) *Sleep* 25:391-398; U.S. patent application Ser. No. 10/472,136).

In view of the fact that the only viable treatment for individuals suffering from sleep-related breathing disorders is a mechanical form of therapy for which patient compliance is low, and that hopes for pharmacological treatments have yet to come to fruition, there remains a need for pharmacologically-based treatments that would offer benefits to a broad base of individuals suffering from a range of sleep-related breathing disorders. There also remains a need for a viable treatment of sleep-related breathing disorders that would have a high rate of patient compliance. The present invention meets this need in the art.

SUMMARY OF THE INVENTION

The present invention is a method for preventing or ameliorating a sleep-related breathing disorder by administering an effective amount of at least one cholecystokinin (CCK) receptor antagonist to a patient in need of such therapy. In particular embodiments, the CCK receptor antagonist is used in combination with at least one other therapeutic agent useful for treating sleep-related breathing disorders.

DETAILED DESCRIPTION OF THE INVENTION

It has now been found that the frequency of apnea expression is significantly reduced in all sleep stages upon administration of a cholecystokinin (CCK) receptor antagonist. Accordingly, the present invention relates to the use of CCK receptor antagonists in the prevention or suppression of sleep-related breathing disorders.

In accordance with the present invention, a sleep-related breathing disorder is a pulmonary disorder that is manifested primarily or exclusively during sleep. This is in contrast to sleep disorders which generally relate to disturbances of sleep that affect the ability to fall and/or stay asleep, e.g., insomnia. Examples of such sleep-related breathing disorders include, but are not limited to, obstructive sleep apnea syndrome, apnea of prematurity, congenital central hypoventilation syndrome, obesity hypoventilation syndrome, central sleep apnea syndrome, Cheyne-Stokes respiration, and snoring. In particular embodiments, the sleep-related breathing disorder of the present invention is central or obstructive sleep apnea. The diagnosis or identification of subjects in need of treatment with a CCK receptor antagonist of the present invention can be carried out using standard methods well-known to the skilled clinician, including polysmonography.

CCK receptors are G-protein coupled receptors that bind members of the cholecystokinin (CCK) family of peptide hormones. As used in the context of the present invention, a CCK receptor is intended to include one or a plurality of CCK A or CCK B receptor subtypes well-known in the art. See, for example, Pisegna, et al. (1992) *Biochem. Biophys. Res. Commun.* 189 (1):296-303; de Weerth, et al. (1993) *Biochem. Biophys. Res. Commun.* 194(2):811-818; Lee, et al. (1993) *J. Biol. Chem.* 268(11):8164-8169; and GENBANK Accession Nos. NP_795344 and NP_000721. The CCK A receptor subtype is a major physiologic mediator of pancreatic enzyme secretion and smooth muscle contraction of the gallbladder and stomach. In the central and peripheral nervous system, the CCK A receptor regulates satiety and the release of beta-endorphin and dopamine. The CCK B receptor is a type B gastrin receptor, which has a high affinity for both sulfated and non-sulfated CCK analogs and is found principally in the central nervous system and the gastrointestinal tract. Thus, in one embodiment, the CCK receptor antagonist has activity in the peripheral nervous system and/or does not cross the blood-brain barrier. In another embodiment, the CCK receptor antagonist exhibits activity against either a CCK A receptor or a CCK B receptor. In still a further embodiment, the CCK receptor antagonist exhibits activity against both CCK A and CCK B receptors.

Exemplary antagonists which exhibit activity toward both CCK A and CCK B receptors include, but are not limited to benzotript and proglumide. Exemplary CCK A receptor antagonists include, but are not limited to, L-364,718 (devazepide); loxiglumide; dexloxiglumide; lorglumide; L-lorglumide; D-lorglumide; PD-140,548; TP-680; T-0632; A-67396; A-70276; A-71134 and SR 27897. Exemplary CCK B receptor antagonists include, but are not limited to, CR2945; YM022; itriglumide; L-740,093; L-365,260; L-156,586; LY-262691; ureidoacetamides (e.g., RP 69758, RP 72540, RP 73870); tetronothiodin; peptide analogs (CI-1015 and CI-988); YF476; A-63387 and GV150013X. Other exemplary CCK receptor antagonists include, but are not limited to, A-64718; A-65186; spiroglumide; CR-2345; CR-2767; CR2622; tarazepide; L-365,260; L-708,474; L-368,730; L-369,466; L-736,380; FK-480; FR175985; FR193108; FR196979; FR202893, FR208418; FR208419; CP212,454; CP310,713; GV191869X; GV199114X; RPR1011367; S-0509; DA-3934; D51-9927; LY-202769; CCK-8; CCK-4; CAM1189; PD-135,666; CAM1481; PD-140,547; PD-140,723; PD-149,164; JB93182; AG-041R; SR-27,897 (linitript); KSG-504; 2-NAP and other CCK receptor antagonists known in the art.

Those of skill in the art also will recognize that with respect to the agents disclosed herein, such agents can contain a center of chirality. Thus, such agents can exist as different enantiomers or as enantiomeric mixtures. Use of any one enantiomer alone or contained within an enantiomeric mixture with one or more stereoisomers is contemplated by the present invention.

As demonstrated herein, the effectiveness of a particular CCK antagonist for preventing or ameliorating a sleep-related breathing disorder can be determined by assessing whether the antagonist inhibits expression of spontaneous apneas during non-rapid eye movement (NREM) sleep and rapid eye movement (REM) sleep in freely moving animals.

Previous studies on the effect of serotonin or serotonin analogs on respiration in several anesthetized animal models have demonstrated inconsistent responses. For example, administration of serotonin has been shown to cause an increase in the respiratory rate with a decrease in tidal volume in rabbits, but an increase in the tidal volume in dogs (Bisgard, et al. (1979) *Respir. Physiol.* 37:61-80; Zucker & Cormish (1980) *Circ. Res.* 47:509-515; Matsumoto (1981) *Arch. Int. Phamacodyn. Ther.* 254:282-292). In studies with cats, serotonin administration produced hyperventilation occasionally preceded by apnea (Jacobs & Comroe (1971) *Circ. Res.* 29:145-155; Black, et al. (1972) *Am. J. Physiol.* 223:1097-1102), or immediate apnea followed by rapid shallow breathing (Szereda-Przestaszewska & Wypych (1995) *Respir. Physiol.* 101:231-237). Intravenous administration of serotonin, 2-methyl-5-hydroxytryptamine or a high dose of α-methyl-5-hydroxytryptamine (a 5-hydroxytryptamine 2 receptor agonist) to anesthetized rats produced immediate apnea with a duration determined by the drug dose; an effect that was blocked by bilateral transection of the vagus nerves above the nodose ganglia (Yoshioka. et al. (1992) *J. Pharmacol. Exp. Ther.* 260:917-924).

These studies revealed that activity at serotonin receptors can initiate reflex apnea, a term that refers to interruption of respiratory effort produced by activation of certain cranial nerve reflexes. One classic example is the so-called diving reflex, in which stimulation of trigeminal nerve fibers by cold water on the face or nasal mucosa produces an apnea that can prevent liquid aspiration. The Hering-Brueur reflex is an apnea produced by inflation of the lungs, and serves to guard against over-inflation injury. Upper airway receptors can trigger apnea in response to inhalation of noxious gases. These latter two forms of reflexive apnea are mediated by the afferent fibers of the vagus nerves. The findings of Yoshioka, et al. ((1992) *J. Pharmacol. Exp. Ther.* 260:917-924) suggest that the vagus nerves also are necessary for intravascular serotonin to evoke reflex apnea. Vagus sensory neurons, which have their cell bodies in the nodose ganglia, carry information to the brain from many receptors distributed throughout the lungs and chest wall. Endogenous CCK, a sulfated octapeptide, is a potent activator of sensory neurons of the vagus nerves. Application of CCK to isolated nodose ganglion cells produces concentration-dependent depolarizations of the afferent neurons (Widdop, et al. (1994) *J. Auton. New. Syst.* 46:65-73), and concentration-response curves of isolated ganglion cells are shifted to the right (i.e., higher CCK concentrations are required to achieve an equivalent effect) by low concentrations of CCK receptor antagonists. Two general classes of CCK receptors have been functionally identified, CCK A and CCK B receptors. The drug devazepide, a CCK A receptor antagonist, is highly potent in blocking CCK-induced depolarization of nodose ganglion neurons (Widdop, et al. (1994) supra). Conversely, the CCK B receptor antagonist LY-365,260 is less potent. These findings may account for blockade of vagus nerve-dependent reflex apnea.

As contemplated herein, any CCK receptor antagonist or combination of antagonists that interferes with the activity of endogenous CCK can be used as an effective treatment for sleep-related breathing disorders. Not wishing to be bound by theory, it is believed that a mechanism for this effect is interference with the activation of vagus sensory neurons by endogenous CCK. However, it was also found that CCK antagonists also protect against spontaneous sleep-related apnea. This result was unexpected, since it is known that vagus-nerve reflex apnea and sleep apnea are different. Reflex apnea occurs because of an external stimulus (e.g., fluid or foreign body aspiration, irritant inhalation, or excessive lung inflation), both in awake and sleeping individuals, whereas sleep apnea occurs spontaneously and specifically during sleep.

In accordance with the instant method, a subject (e.g., human or companion, zoological, or agricultural animal) diagnosed with a sleep-related breathing disorder is administered a CCK receptor antagonist, or pharmaceutical composition containing said antagonist, in an amount effective to prevent or ameliorate such disorders. Generally, pharmaceutical compositions contain the active agent in admixture with one or more suitable carriers or vehicles, wherein the pharmaceutical composition is formulated based upon, for example, the intended route of administration, delivery format and desired dosage. See e.g., Remington: The Science and Practice of Pharmacy, Alfonso R. Gennaro, editor, 20th ed. Lippincott Williams & Wilkins: Philadelphia, Pa., 2000.

The primary vehicle or carrier in a pharmaceutical composition can be either aqueous or non-aqueous in nature. For example, a suitable vehicle or carrier can be water for injection, physiological saline solution or artificial cerebrospinal fluid, possibly supplemented with other materials common in compositions for parenteral administration. Neutral buffered saline or saline mixed with serum albumin are further exemplary vehicles. Pharmaceutical compositions can contain Tris buffer of about pH 7.0-8.5, or acetate buffer of about pH 4.0-5.5, which can further include sorbitol or a suitable substitute thereof. Pharmaceutical compositions of the invention can be prepared for storage by mixing the selected composition having the desired degree of purity with optional formulation agents in the form of a lyophilized cake or an aqueous solution. Further, the compositions can be formulated as a lyophilizate using appropriate excipients such as sucrose.

Acceptable formulation materials preferably are nontoxic to recipients at the dosages and concentrations employed. The pharmaceutical composition can contain formulation materials for modifying, maintaining or preserving, for example, pH, osmolarity, viscosity, clarity, color, isotonicity, odor, sterility, stability, rate of dissolution or release, adsorption or penetration of the composition. Suitable formulation materials include, but are not limited to, amino acids (such as glycine, glutamine, asparagine, arginine or lysine); antimicrobials; antioxidants (such as ascorbic acid, sodium sulfite or sodium hydrogen-sulfite); buffers (such as borate, bicarbonate, Tris-HCl, citrates, phosphates or other organic acids); bulking agents (such as mannitol or glycine); chelating agents (such as ethylenediamine tetraacetic acid (EDTA)); complexing agents (such as caffeine, polyvinylpyrrolidone, beta-cyclodextrin or hydroxypropyl-beta-cyclodextrin); fillers; monosaccharides, disaccharides, and other carbohydrates (such as glucose, mannose or dextrins); proteins (such as serum albumin, gelatin or immunoglobulins); coloring, flavoring and diluting agents; emulsifying agents; hydrophilic polymers (such as polyvinylpyrrolidone); low molecular weight polypeptides; salt-forming counterions (such as sodium); preservatives (such as benzalkonium chloride, benzoic acid, salicylic acid, thimerosal, phenethyl alcohol, methylparaben, propylparaben, chlorhexidine, sorbic acid or hydrogen peroxide); solvents (such as glycerin, propylene glycol or polyethylene glycol); sugar alcohols (such as mannitol or sorbitol); suspending agents; surfactants or wetting agents (such as PLURONICS, PEG, sorbitan esters, polysorbates such as polysorbate 20 and polysorbate 80, TRITON, trimethamine, lecithin, cholesterol, or tyloxapal); stability enhancing agents (such as sucrose or sorbitol); tonicity enhancing agents (such as alkali metal halides, preferably sodium or potassium chloride, mannitol, or sorbitol); delivery vehicles; diluents; excipients and/or pharmaceutical adjuvants.

Routes of administration can be by any system means including oral, intraperitoneal, subcutaneous, intravenous, intramuscular, transdermal, inhaled, or by other routes of administration; osmotic mini-pumps and timed-released pellets or other depot forms of administration can also be used. Pharmaceutical compositions can be administered by bolus injection or continuously by infusion, or by implantation device. Pharmaceutical compositions also can be administered locally via implantation of a membrane, sponge or another appropriate material onto which the desired antagonist has been absorbed or encapsulated. Where an implantation device is used, the device can be implanted into any suitable tissue or organ, and delivery of the desired antagonist can be via diffusion, timed-release bolus, or continuous administration. The only limitation for administration route according to the methods of this invention is that the route of administration results in the ultimate delivery of the pharmacological agent to the appropriate receptor.

When parenteral administration is contemplated, the pharmaceutical composition for use in this invention can be in the form of a pyrogen-free, parenterally acceptable aqueous solution containing the desired antagonist in a pharmaceutically acceptable vehicle. A particularly suitable vehicle for parenteral injection is sterile distilled water. Preparation can involve the formulation of the desired antagonist into a carrier, such as injectable microspheres, bio-erodible particles, polymeric compounds (such as polylactic acid or polyglycolic acid), beads or liposomes, to provide controlled or sustained release of the antagonist. Formulation with hyaluronic acid can also have the effect of promoting sustained duration in the circulation.

An antagonist of the invention can also be formulated as a dry powder for inhalation, or as an inhalation solution with a propellant for aerosol delivery, such as by nebulization. Pulmonary administration is further described in PCT Application No. PCT/US94/001875.

Oral delivery is also contemplated, wherein an antagonist of the invention is formulated with or without a carrier customarily used in the compounding of solid dosage forms such as tablets and capsules. A capsule can be designed to release the active ingredient of the formulation at the point in the gastrointestinal tract when bioavailability is maximized and pre-systemic degradation is minimized. Additional agents such as diluents, flavorings, low melting point waxes, vegetable oils, lubricants, suspending agents, tablet disintegrating agents, and binders can also be employed.

Tablets are generally formulated by mixing an effective quantity of an antagonist as disclosed herein with one or more non-toxic excipients that are suitable for the manufacture of tablets. Suitable excipients include, but are not limited to, inert diluents, such as calcium carbonate, sodium carbonate or bicarbonate, lactose, or calcium phosphate; or binding agents, such as starch, gelatin, or acacia; or lubricating agents such as magnesium stearate, stearic acid, or talc.

Additional pharmaceutical compositions are evident to those skilled in the art, including formulations involving appropriate CCK receptor antagonists as disclosed herein in sustained- or controlled-delivery formulations. Techniques for formulating a variety of sustained- or controlled-delivery means, such as liposome carriers, bio-erodible microparticles or porous beads and depot injections, are also known to those skilled in the art. See, for example, PCT Application No. PCT/US93/00829, which describes the controlled release of porous polymeric microparticles for the delivery of pharmaceutical compositions. Sustained-release preparations can include semi-permeable polymer matrices in the form of shaped articles, e.g., films, or microcapsules, polyesters, hydrogels, polylactides (e.g., U.S. Pat. No. 3,773,919), copolymers of L-glutamic acid and gamma ethyl-L-glutamate (Sidman, et al. (1983) *Biopolymers* 22:547-556), poly (2-hydroxyethyl-methacrylate) (Langer, et al. (1981) *J. Biomed. Mater. Res.* 15:167-277; Langer (1982) *Chem. Tech.* 12:98-105), ethylene vinyl acetate or poly-D(−)-3-hydroxy-butync acid (EP 133,988). Sustained-release compositions can also include liposomes, which can be prepared by any of several methods known in the art. See, e.g., Eppstein, et al. (1985) *Proc. Natl. Acad. Sci. USA* 82:3688-3692.

Pharmaceutical compositions for use in vivo are typically sterile. In certain embodiments, this can be accomplished by filtration through sterile filtration membranes. In other embodiments, where the composition is lyophilized, sterilization can be conducted either prior to or following lyophilization and reconstitution. Once a pharmaceutical composition has been formulated, it can be stored in sterile vials as a solution, suspension, gel, emulsion, solid, or as a dehydrated or lyophilized powder. Such formulations can be stored either in a ready-to-use form or in a form (e.g., lyophilized) that is reconstituted prior to administration.

This invention further provides kits for producing a single-dose administration unit. Kits according to the invention can each contain both a first container having a dried antagonist as disclosed herein and a second container having an aqueous formulation, including for example single and multi-chambered pre-filled syringes (e.g., liquid syringes, lyosyringes or needle-free syringes).

An effective amount of an antagonist of the invention to be employed therapeutically will depend, for example, upon the therapeutic context and objectives. One skilled in the art will appreciate that the appropriate dosage levels for treatment, according to certain embodiments, will thus vary depending, in part, upon the antagonist delivered, the indication for which the antagonist is being used, the route of administration, and the size (body weight, body surface or organ size) and/or condition (the age and general health) of the subject. In accordance with the present methods, the prevention or amelioration of a sleep-related breathing disorder generally has the clinical outcome of delaying or preventing apneic episodes or decreasing the number, frequency, or duration of apneic episodes. A clinician can titer the dosage and modify the route of administration to obtain the optimal therapeutic effect. Typical dosages range from about 0.1 µg/kg to up to about 100 mg/kg or more, depending on the factors mentioned above.

Dosing frequency will depend upon the pharmacokinetic parameters of an antagonist as disclosed herein in the formulation. For example, a clinician administers the antagonist until a dosage is reached that achieves the desired effect. As such, the antagonist can be administered as a single dose, or as two or more doses (which may or may not contain the same amount of the desired antagonist) over time, or as a continuous infusion via an implantation device or catheter. Further refinement towards establishing an appropriate dosage is routinely made by those of ordinary skill in the art. Appropriate dosages can also be ascertained through use of appropriate dose-response data.

Administration to a subject in need of treatment can be carried out immediately before sleep or at any time prior to sleep with the appropriate slow release or delayed release dosage forms as required for the circumstances. The effect of such treatment will be the alleviation, amelioration, suspension, and/or cessation of the sleep-related breathing disorder(s) of the subject.

CCK receptor antagonists of the present invention can be administered alone or in combination with other one or more therapeutic agents, in particular, in combination with other agents for treating sleep disorders or sleep-related breathing disorders. In some embodiments, the instant antagonist is co-administered (i.e., simultaneously or consecutively) with sleep-inducing compounds or barbiturates, and the like. In other embodiments, the instant antagonist is administered in combination with at least one other sleep-related breathing disorder therapeutic agent, including but not limited to, serotonin receptor agonists, serotonin receptor antagonists, serotonin release promoters, serotonin reuptake inhibitors, noradrenaline reuptake inhibitors, combined serotonin/noradrenaline reuptake inhibitors, glutamate receptor antagonists, glutamate release inhibitors, glutamate reuptake promoters and cannabimimetic agents including cannabinoid receptor agonists, cannabinoid promoters, cannabinoid membrane transport inhibitors and endocannabinoid breakdown inhibitors, or combinations thereof.

Accordingly, one embodiment of the present invention embraces the use of a single agent or combination of agents having either CCK A or CCK B receptor subtype antagonistic activity or both. Another embodiment embraces the use of a single agent or combination of agents having either CCK A or CCK B subtype antagonistic activity or both in conjunction with either a selective serotonin re-uptake inhibitor (SSRI) or serotonin/noradrenaline reuptake inhibitor (SNRI) activity or both. A further embodiment embraces the use of a single agent or combination of agents having either CCK A or CCK B subtype antagonistic activity or both in conjunction with a serotonin receptor agonist. Another embodiment embraces the use of a single agent or combination of agents having either CCK A or CCK B subtype antagonistic activity or both in conjunction with a serotonin receptor antagonist. A further embodiment embraces the use of a single agent or combination of agents having either CCK A or CCK B subtype antagonistic activity or both in conjunction with a serotonin release promoter. A still further embodiment provides for the use of a single agent or combination of agents having either CCK A or CCK B subtype antagonistic activity or both in conjunction with either a cannabinoid receptor subtype 1 or cannabinoid receptor subtype 2 agonist, or both. In yet another embodiment, a single agent or combination of agents having either CCK A or CCK B subtype antagonistic activity or both is used in conjunction with an endocannabinoid breakdown inhibitor (e.g., a fatty acid amide hydrolase inhibitor) or membrane transport inhibitor. It is contemplated that any combination of agents and any number of agents can be used in conjunction with a CCK receptor antagonist of the present invention. By way of illustration, an example of combination therapy can include the use of a CCK A receptor antagonist, a CCK B receptor antagonist, a serotonin reuptake inhibitor and two cannabinoid receptor agonists. As another illustrative example, a combination therapy can include a CCK A/B receptor antagonist, a combined serotonin/noradrenaline reuptake inhibitor, and an endocannabinoid breakdown inhibitor.

Exemplary serotonin receptor agonists include, but are not limited to, 8-OH-DPAT, almotriptan, sumatriptan, L694247 (2-[5-[3-(4-methylsulphonylamino)benzyl-1,2,4-oxadiazol-5-yl]-33 1H-indol-3yl]ethanamine), tegaserod, buspirone, ainitidan, zaiospirone, ipsapirone, gepirone, zolmitriptan, elitriptan, naratriptan, frovatriptan, rizatriptan, a-Me-5-HT, BW723C86 (1-[5(2-thienyhethoxy)-1H-3-indolyl[propan-2-amine hydrochloride), MCPP (m-chlorophenylpiperazine), MK-212, bufotenin, 1-(m-trifluoromethylphenyl)-piperazine, N,N-dimethyl-5-methoxytryptamine, quipazine, venlafaxine, bifeprunox, donitriptan, and other serotonin agonists.

Exemplary serotonin receptor antagonists include, but are not limited to ondansetron (GR38032F), ketanserin, risperidone, cyproheptadine, clozapine, methysergide, granisetron, mianserin, ritanserin, cinanserin, LY-53,857, metergoline, LY-278,584, methiothepin, p-NPPL, NAN-190, piperazine, SB-206553, SDZ-205,557, 3-tropanyl-indole-3 carboxylate, 3-tropanyl-indole-3-carboxylate methiodide, and other serotonin receptor antagonists.

Exemplary glutamate receptor antagonists include, but are not limited to D-AP5 (D(−)-2-amino-5-phosphonopentanoate), CGS19755 (4-phosphonomethyl-2-piperidine carboxylic acid), CGP37849 (D,L-(E)-2-amino-4-methylphosphono-3-pentanoic acid), LY233053 (cis-(.+-.)-4-(2H-tetrazol-5-yl)methyl-piperidine-2-carboxylic acid), AIDA (1-aminoindan-1,5(RS)-dicarboxylic acid), (S)-(+)-CBPG ((s)-(+)-2-(3'-carboxy-bicyclo(1.1.1.)pentyl)glycine), CPCCOEt (cyclopropan(b)chromen-1a-carboxylate), EGLU ((s)-(.alpha.)-ethylglutamate), LY307452 (2s,4s-2-amino-4-(4,4-diphenylbut-1-yl)pentan-1,5-dioc acid) LY341495 (2s-2-amino-2-(1s,2s-2-carboxy-cyclopropan-1-yl)-3-(xanth-9-yl)propanoic acid), PCCG-4 (2s,1's,2's,3'R)-2-(2'-carboxy-3'-phenylcyclopropyl)glycine), 4-CPG (4-carboxyphenylglycine), memantine, and amantadine.

Exemplary inhibitors of glutamate release include, but are not limited to, lamotrigine, BW1003C87, riluzole, isoguvacine, muscimol, THIP, piperidine-4-sulphonic acid, flunitrazepam, zolpidem, abecarnil, ZK93423, L-baclofen, CGP27492, piracetam, progabide, and CGP35024.

Exemplary glutamate reuptake promoters include but are not limited to zonisamide.

Exemplary serotonin reuptake inhibitors include, but are not limited to, fluoxetine, norfluoxetine, R(+)-fluoxetine, S(−)-fluoxetine, paroxetine, zimelidine, pirandamine, fluvoxamine, citalopram, escitalopram, ORG6582, p-bromo EXP561, LM5008, sertraline, and other serotonin reuptake inhibitors.

Exemplary noradrenaline reuptake inhibitors include, but are not limited to, desipramine, nortriptyline, reboxetine, nisoxetine, atomoxetine, LY 139603 (tomoxetine), and other noradrenaline reuptake inhibitors.

Exemplary combined serotonin/noradrenaline reuptake inhibitors include, but are not limited to, venlafaxine, milnacipran, duloxetine, pregabalin, LY248686, strattera, and other combined serotonin/noradrenaline reuptake inhibitors.

Exemplary cannabimimetic agents include cannabinoid receptor agonists including, but not limited to, arachidonyl-2'-chloroethylamide, arachidonylcyclo-propylamide, methanandamide, L-759633, L-759656, JWH-133, Hu-308, and palmitoylethanolamide, 9-tetrahydrocannabinol, 8-tetrahydrocannabinol, HU-210, CP55940, 2-arachidonoyl glycerol, anandamide, dexanabinol, nabilone, levonantradol, and N-(2-hydroxyethyl)hexadecanoamide; endocannabinoids including, but not limited to, oleamide, linoleoylethanolamide, and oleoylethanolamide; endocannabinoid breakdown inhibitors including, but not limited to, phenylmethylsulphonyl fluoride, palmitylsulphonyl fluoride, stearylsulphonyl fluoride, methyl arachidonyl fluorophosphonate, 2-octyl-gamma-bromoacetoacetate, ibuprofen, ketorolac, and flurdiprofen and 0-1887; and endocannabinoid membrane transport inhibitors including, but not limited to, AM404, VDM11, and arvanil.

The instant CCK receptor antagonist can be administered in co-formulation with these other agents or alternatively separate pharmaceutical compositions can be prepared and administered in accordance with the instant disclosure. In particular embodiments, co-administration encompasses use of an agent or combination of agents exhibiting either CCK A or CCK B receptor antagonism (either alone or in combination with one another) in combination with an agonist for either 5-hydroxytryptamine-1 or 5-hydroxytryptamine-2 receptors, or both. In other embodiments, co-administration encompasses use of an agent or combination of agents that exhibit both CCK A and CCK B receptor antagonism in combination with an agonist for either 5-hydroxytryptamine-1 or 5-hydroxytryptmine-2 receptors, or both. In embodiments drawn to the use of one or more serotonin agonists, it is contemplated that the agent or combination of agents exhibit only central serotonergic actions or alternatively exhibit only central 5-hydroxytryptamine-2 actions. In accordance with another embodiment, an agent or combination of agents is used, wherein the CCK receptor antagonist exhibits only peripheral actions while the serotonin agonist exhibits only central actions.

In another embodiment, co-administration encompasses use of an agent or combination of agents exhibiting either CCK A or CCK B receptor antagonism (either alone or in combination with one another) in combination with a cannabimimetic agent. In still further embodiments, co-administration encompasses use of an agent or combination of agents that exhibit both CCK A and CCK B receptor antagonism in combination with a cannabimimetic agent. In embodiments drawn to the use of one or more cannabimimetic agents, it is contemplated that the agent is a cannabinoid CB1 receptor agonist, a cannabinoid CB2 receptor agonist, a non-selective cannabinoid receptor agonist, an endocannabinoid, an inhibitor of cannabinoid breakdown, an inhibitor of endocannabinoid membrane transport, or a cannabinoid precursor or prodrug or both.

In a still further embodiment, co-administration encompasses use of an agent or combination of agents that have the ability to induce central nervous system serotonin and/or noradrenaline release in combination with CCK A and/or a CCK B receptor antagonist. In accordance with this embodiment, it is contemplated that said agents have the ability to induce central nervous system serotonin and/or noradrenaline release and possess only peripheral antagonistic effects. In still other embodiments, co-administration encompasses the use of an agent or combination of agents that have the ability to inhibit reuptake of serotonin and/or noradrenaline in combination with CCK A and/or a CCK B receptor antagonist.

The following examples illustrate the analysis of the effects of CCK receptor antagonist administration, and in particular the ability of these antagonists to cause suppression of spontaneous apneas during NREM and especially during REM sleep. The following examples also illustrate testing of the capacity of CCK agonists to induce spontaneous apnea expression, and the ability of CCK antagonists to block this effect. The following examples further describe the pharmacological profiles best suited for single agents or combinations of agents to successfully prevent or ameliorate sleep-related breathing disorders.

The invention is described in greater detail by the following non-limiting examples.

Example 1

Animal Model

This example describes how experimental animals are prepared for treatment with either CCK receptor antagonists, alone or in combination with other agents, and subsequent physiological recording and testing.

Adult, male Sprague-Dawley rats (Sasco-King, Wilmington, Mass.), usually 8 per test group with an average weight of 300 grams, are maintained on a 12-hour light/12-hour dark cycle for one week. The animals are housed in individual cages and given ad libitum access to food and water. Following the one week of acclimatization, animals are subjected to the following surgical procedures.

Acclimatized animals are anesthetized using a mixture of ketamine (80 mg/kg) and xylazine (5 mg/kg) at a volume of 1 ml/kg body weight for the implantation of cortical electrodes for electroencephalogram (EEG) recording and neck muscle electrodes for electromyogram (EMG) recording. The surface of the skull is exposed surgically and cleaned with a 20% solution of hydrogen peroxide followed by a solution of 95% isopropyl alcohol. A dental preparation of sodium fluoride (FLURA-GEL; Saslow Dental, Mt. Prospect, Ill.) is subsequently applied to harden the skull above the parietal cortex and allowed to remain in place for 5 minutes. The fluoride mixture is then removed from the skull above the parietal cortex. The EEG electrodes consisting of four stainless steel machine screws, having leads attached thereto, are threaded into the skull to rest on the dura over the parietal cortex. A thin layer of JUSTI resin cement (Saslow Dental, Mt. Prospect, Ill.) is applied to cover the screw heads (of screws implanted in the skull) and surrounding skull to further promote the adhesion of the implant. EMG electrodes consisting of two ball-shaped wires are inserted into the bilateral neck musculature. All leads (i.e., EEG and EMG leads) are soldered to a miniature connector (39F1401; Newark Electronics, Schaumburg, Ill.). The entire assembly is subsequently fixed to the skull with dental cement.

After surgery, all animals are allowed to recover for one week before being recorded for sleep and breathing.

Example 2

Physiological Recording and Apnea Suppression

This example describes physiological recording methods used in treated and control animals and interpretation of results obtained from administration of a CCK antagonist.

Physiological parameters from each animal prepared as described herein are recorded on two to five occasions in random order, with recordings for an individual animal separated by at least 3 days. Fifteen minutes prior to each recording an animal receives a systemic injection (1 mL/kg intraperitoneal bolus) of either saline (control) or an active dose of a drug treatment.

Respiration is recorded by placing each animal, unrestrained, inside a single chamber plethysmograph (PLY-UNIR/U; Buxco Electronics, Sharon, Conn.; dimension 6 inches×10 inches×6 inches) ventilated with a bias flow of fresh room air at a rate of 2 Liters/minute. A cable plugged onto the animal's connector and passed through a sealed port is used to collect the bioelectrical activity from the head implant. Respiration, EEG activity, and EMG activity are displayed on a video monitor and simultaneously digitized 100 times per second and stored on computer disk (Experimenter's Workbench; Datawave Technologies, Longmont, Colo.).

Sleep and waking states are assessed using conventional software (Benington, et al. (1994) *Sleep* 17:28-36) to analyze the biparietal EEG and nuchal EMG signals on 10-second epochs. The software discriminates wakefulness (W) as a high frequency low amplitude EEG with a concomitant high EMG tone, NREM sleep by increased spindle and theta activity together with decreased EMG tone, and REM sleep by a low ratio of a delta to theta activity and an absence of EMG tone. Sleep efficiency is measured as the percentage of total recorded epochs staged as NREM or REM sleep.

An accepted physiological animal model of spontaneous sleep apnea in the rat (see Radulovacki & Carley (2002) In: *Sleep-Related Breathing Disorder: Experimental Models and Therapeutic Potential* (Carley & Radulovacki, eds.) Marcel Dekker: New York, pp. 3-16) is used to assess the effects of test drugs. More specifically, sleep apneas, defined as cessation of respiratory effort for at least 2.5 seconds, are scored for each recording session and associated with the stage of sleep in which they occur (i.e., NREM or REM sleep). The duration requirement of 2.5 seconds represents at least two "missed" breaths, which is therefore analogous to a 10 second apnea duration requirement in humans, which also reflects two to three missed breaths. The events detected represent central apneas because decreased ventilation associated with obstructed or occluded airways would generate an increased plethysmographic signal, rather than a pause. Apnea indexes (AI), defined as apneas per hour in a stage are separately determined for NREM and REM sleep. The effects of sleep stage (NREM vs. REM) and injection (control vs. dose of active test drug) are tested using ANOVA with repeated measures. Multiple comparisons are controlled using Fisher's protected least significant difference (PLSD) test. In addition, the timing and volume of each breath are scored by automatic analysis (Experimenter's Workbench; Datawave Technologies, Longmont, Colo.). For each animal the mean respiratory rate (RR) and minute ventilation (MV) are computed for W (wakefulness) throughout the 6-hour control recording and used as a baseline to normalize respiration during sleep and during active drug administration in that animal. One-way ANOVA is also performed by non-parametric (Friedman) analysis. Conclusions using parametric and non-parametric ANOVA are compared in all cases.

Results of the administration of the CCK receptor antagonist on the rate of apneas per hour of NREM and REM sleep during the 6 hours of polygraphic recording that demonstrate a significant suppression ($p<0.05$) are indicative of efficacy against sleep apnea and other sleep-related breathing disorders. According to this approach, devazepide, lorglumide, and L-365,260 all demonstrate dose-dependent efficacy against sleep apnea.

Moreover, using the above-describe approach, sleep and breathing (plethysmograph) recordings were obtained on five occasions (separated by at least 3 days) for rats receiving a sham injection (i.p. DMSO 1 mL/kg) or 0.005, 0.05, 0.5 or 5.0 mg/kg CR2945 (in DMSO). Injection sequence was randomized in each animal and sleep was staged on 10 second epochs, wherein apneas (pauses>2.0 seconds) were associated with sleep stage of occurrence and according to the presence (post-sigh, PS) or absence (spontaneous, SP) of an immediately preceding sigh. It was observed that sleep architecture was unchanged from baseline by any dose of CR2945 (p>0.1 for % W, % NREM and % REM for each dose versus sham). SP apnea index was reduced to 42% and 31% of placebo value by the 0.5 and 5.0 mg/kg doses, respectively (p<0.03 for each), but apnea duration was not affected by any dose (p=0.7). Similar reductions were observed for NREM SP apnea index (p<0.05 for 0.5 and 5.0 mg/kg). REM SP apnea index was significantly reduced by all four doses of CR2945 tested (p<0.04 for each). Thus, the frequency of spontaneous central apnea expression was significantly reduced in all sleep stages in rats given a systemic injection of CR2945. Thus, those of skill in the art will recognize that other CCK receptor antagonists can be used to prevent or ameliorate sleep-related breathing disorders. Further, those of skill in the art will also recognize that the results that are obtained using this animal model can be readily correlated to other mammals, especially primates (e.g., humans).

Example 3

Induction and Suppression of Sleep Apneas

This example describes the interpretation of results that can be obtained from experimental animals first treated by CCK agonist administration followed by CCK receptor antagonist administration.

Administration of CCK antagonists or CCK agonists alone and in combination to produce respiratory responses in anesthetized animals is performed as disclosed herein. An increased rate of sleep apneas after a CCK agonist and a blockade of this effect by treatment with a CCK antagonist is indicative of the therapeutic efficacy of the antagonist to treat sleep apnea and other sleep-related breathing disorders.

Overall, exacerbation of spontaneous apnea during sleep produced by peripherally administered CCK agonists and a blockade of this effect by CCK antagonists indicate a physiological role for CCK in regulating breathing and therapeutic efficacy of treating sleep apnea by CCK antagonists.

Example 4

Suppression of Sleep Apneas by a CCK Antagonist in Combination with a Second Agent Administration of CCK antagonists alone and in combination with other agents (e.g., including, but not limited to, serotonin agonists, cannabimimetics, SSRIs, or SNRIs) to produce respiratory responses in anesthetized animals is performed described herein. Isobolographic analysis is used as an accepted, art-recognized and definitive standard for detecting and characterizing drug interactions (Luszczki & Cmczwar (2003), Epilepsy Res. 56:27-42). An "interaction index" has been proposed (Tallarida (2002) Pain 98:163-168) to quantify drug synergism, and this index is also useful to characterize synergism when one of the two compounds lacks independent efficacy (e.g., an SSRI, see Kraiczi, et al. (1999) Sleep 22:61-66). Isobolographic analysis and the interaction index rely on statistical estimation of the $ED_{50}$. Thus, it is important to have adequate power in the preclinical tests to confidently measure a 50% reduction in apnea expression. For this form of efficacy determination, dose-dependent changes in sleep apnea expression are determined for each agent (i.e., the CCK antagonist and the second agent) alone and combined in various ratios.

A decreased rate of sleep apneas after administration of any formulation (containing one or a combination of CCK receptor antagonists alone or in combination with serotonin agonists, cannabimimetics, SSRIs, or SNRIs as disclosed above) is indicative of the therapeutic efficacy of the formulation to treat sleep apnea and other sleep-related breathing disorders. In particular, a desirable combination of agents exhibits greater suppression of apneas than either agent alone, or equivalent suppression of apneas at lower doses than either agent alone.

Example 5

Suppression or Prevention of Sleep Apneas

As indicated by the examples above, CCK plays an important role in apnea genesis. More specifically, the nodose ganglia of the vagus nerves appear to be a crucial target site for CCK A and CCK B receptor antagonists.

Therefore, in view of the foregoing, sleep-related breathing disorders (sleep apnea syndrome, apnea of infancy, Cheyne-Stokes respiration, sleep-related hypoventilation syndromes) can be effectively prevented or suppressed via systemic administration of pharmacological agents exhibiting either CCK A or CCK B receptor antagonism, alone or in combination, as well as exhibiting both CCK A and CCK B receptor antagonism.

Effective treatment for the prevention or suppression of sleep-related breathing disorders can include, but is not limited to, systemic and local administration of one or a combination of CCK A receptor antagonists, or one or a combination of CCK B receptor antagonists, or a CCK A receptor antagonist and a CCK B receptor antagonist. Such CCK A and CCK B receptor antagonists can be administered in combination with one or more of the other compounds disclosed herein, including, but not limited to, serotonin re-uptake inhibitors (SSRI) or serotonin/noradrenaline reuptake inhibitors (SNRI), serotonin receptor agonists, serotonin receptor antagonists, glutamate receptor antagonists, glutamate release inhibitors, glutamate reuptake promoters, compounds with cannabinoid receptor subtype 1 or cannabinoid receptor subtype 2 activity, endocannabinoid breakdown inhibitors, cannabimimetic agents, and the like. Desirably, the compounds have activity in the peripheral nervous system and do not cross the blood-brain barrier.

Pharmacological treatments other than CCK receptor antagonism can also be used to enhance CCK receptor antagonism (see e.g. U.S. Pat. No. 6,331,536). Specifically, antagonism of presynaptic $\alpha_2$ adrenergic receptors located on brain stem serotonergic neurons (heteroreceptors) enhances serotonin release. Selective receptor antagonists have been shown to block presynaptic and postsynaptic receptors (see e.g., de Boer (1996) J. Clin. Psychiatry 57:19-25; Devane (1998) J. Clin. Psychiatry 59:85-93; Puzantian (1998) Am. J. Health Syst. Pharm 55:44-49; and the like). Central serotonin release is increased with minimal adrenergic side effects, such as hypertension, because the affinity of such agents for central $\alpha_2$ receptors is about 10 times higher than for peripheral $\alpha_2$ receptors. Therefore, because these agents are high affinity antagonists at 5-hydroxytryptamine $_{2A}$, 5-hydroxytryptamine $_{2C}$, and 5-hydroxytryptamine $_3$ receptors, the net effect is increased post-synaptic 5-hydroxytryptamine $_1$ activity within the brain and reduced 5-hydroxytryptamine $_2$ and 5-hydroxytryptamine $_3$ post-synaptic activity in the central and peripheral nervous systems. Each of these pharmacological effects serves to stimulate respiration and suppress apnea.

What is claimed is:

1. A method for ameliorating sleep apnea comprising administering an effective amount of cholecystokinin (CCK) receptor B antagonist:

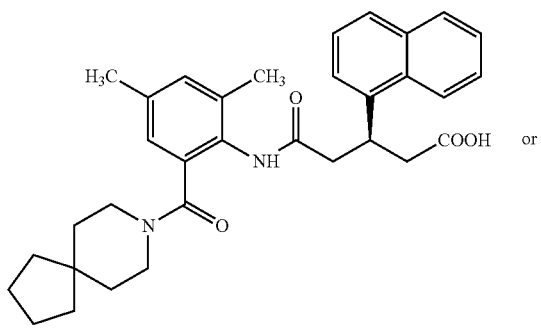

CR2945,

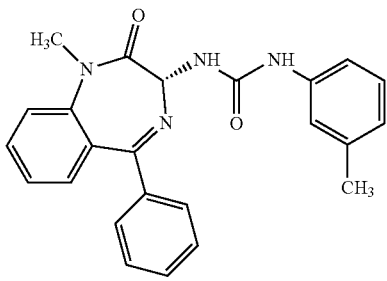

L-365,260,

CR2945, or L-365,260, to a subject in need of treatment thereby ameliorating the subject's sleep apnea.

* * * * *